United States Patent
Deshpande et al.

(10) Patent No.: US 6,800,755 B2
(45) Date of Patent: Oct. 5, 2004

(54) PROCESS FOR THE PREPARATION OF CEFIXIME

(75) Inventors: Pandurang Balwant Deshpande, Chennai (IN); Gautam Kumar Das, Chennai (IN); Pramod Narayan Deshpande, Chennai (IN); Ramasubbu Chandrasekaran, Chennai (IN); Padmanabhan Ramar, Thirunelvelli (IN); John Muthiah Raja Jeyakumar, Chenagalpattu (IN)

(73) Assignee: Orchid Chemicals and Pharmaceuticals Limited, Chennai (IN)

( * ) Notice: Subject to any disclaimer, the term of this patent is extended or adjusted under 35 U.S.C. 154(b) by 0 days.

(21) Appl. No.: 10/310,177

(22) Filed: Dec. 5, 2002

(65) Prior Publication Data

US 2004/0082560 A1 Apr. 29, 2004

(30) Foreign Application Priority Data

Oct. 24, 2002 (IN) .................................... 785/MAS/2002

(51) Int. Cl.[7] .......................................... C07D 510/22
(52) U.S. Cl. ...................................................... 540/222
(58) Field of Search ......................................... 540/222

(56) References Cited

FOREIGN PATENT DOCUMENTS

WO    WO 200198309 A1 * 12/2001 ......... C07D/277/40

OTHER PUBLICATIONS

Translation of WO 01/98309.*

* cited by examiner

*Primary Examiner*—Mark L. Berch

(74) *Attorney, Agent, or Firm*—Oliff & Berridge, PLC

(57) ABSTRACT

The present invention provides an improved process for the preparation of cefixime of formula (I), with an improved quality having/possessing better color and solubility:

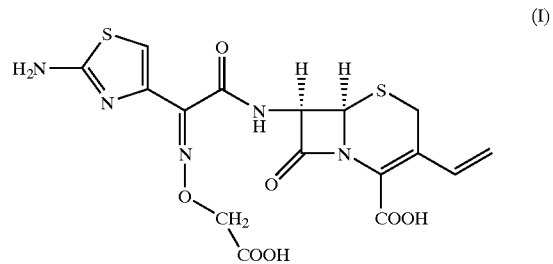

(I)

the process includes the steps of dissolving the compound of formula (II)

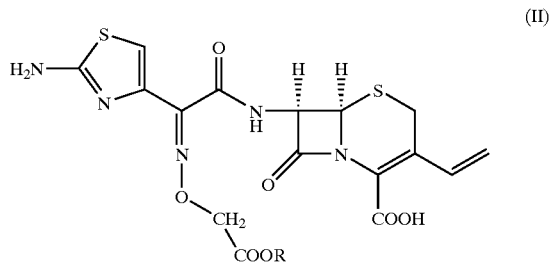

(II)

in water/water immisible solvent using sodium bicarbonate at a temperature in the range of 0° C. to the 35° C., hydrolyzing with sodium hydroxide at a temperature in the range of 0° C. to 25° C., and acidifying the resultant mass to 2.3 to 3.0 with dilute acid in the presence or absence of solvent at a temperature in the range of 10° C. to 45° C.

8 Claims, No Drawings

PROCESS FOR THE PREPARATION OF CEFIXIME

FIELD OF THE INVENTION

The present invention relates to an improved process for the preparation of an orally active cephalosporin antibiotic. The present invention more particularly relates to an improved process for the preparation of cefixime of the formula (I).

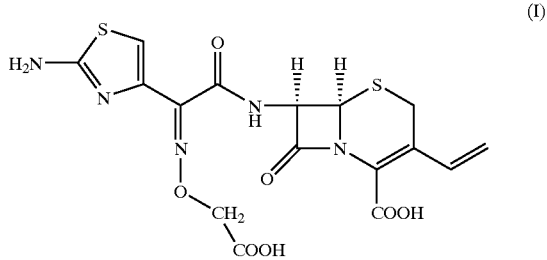

DESCRIPTION OF THE PRIOR ART

Cefixime is an orally active third-generation cephalosporin antibiotic and is more potent against gram-negative bacteria. International publication No 99/51607 and U.S. Pat. No. 4,409,214 discloses the process for the preparation of the cefixime of the formula (I), which involves condensation of 7-amino-3-vinyl-3-cephem-4-carboxylic acid with the derivative of (Z)-2-amino-α-(1-alkoxycarbonylmethoxyimino)-4-thiazole acetic acid to produce ester compound of formula (II),

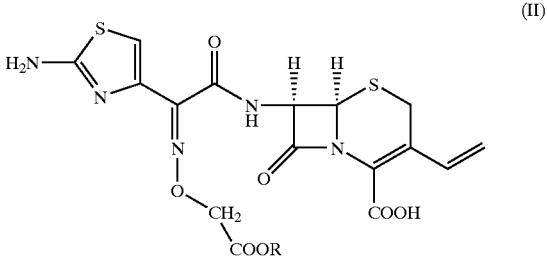

wherein R represents ($C_1$–$C_4$) alkyl group; followed by hydrolysis to produce cefixime of the formula (I).

GB 2 330 140 discloses a process for the preparation of cefixime of formula (I) which comprises treating the compound of formula (II) with $Na_2CO_3$ in DMF and water, which has the following problems: (i) color and quality are poor, (ii) fails in residual solvent i.e. DMF.

GB 2 330 141 discloses a process for the preparation of the compound of formula (I) which comprises treating the compound of formula (II) in an organic solvent with aqueous solution of $Na_2CO_3$ and phase transfer catalyst. The color, quality and yield of the product obtained from bi-phasic reaction are poor.

In U.S. Pat. No. 4,409,214 and WO 95/33753 discloses the process for the preparation of cefixime in which the hydrolysis step involves the use of hazardous trifluoroacetic acid and anisole. In WO 99/52913 the hydrolysis step along with deblocking the amino protective group and carboxylate protective group involves the use of phenol and protonic acid. The steps described in the above patents are more complicated and also suffer from low yield and poor quality.

J. Antibiotics (1985), 38, 1738 discloses various processes for the preparation of cefixime of formula (I). The processes involve the use of column chromatography for purification thereby suffers in poor yield. Column purification cannot be used in large-scale operations, there by making the process commercially not viable.

We have now achieved an improved process for the preparation of the cefixime of the formula (I), which has advantages over the processes, described in the above-mentioned prior art documents.

OBJECTIVES OF THE INVENTION

The main objective of the present invention is to provide an improved process for the preparation of cefixime of the formula (I), which has better quality such as color and solubility.

Another objective of the present invention is to provide an improved process for the preparation of cefixime of the formula (I), which avoids the use of hazardous chemicals like TFA and also easy to implement on commercial scales.

Still another objective of the present invention is to provide an improved process for the preparation of cefixime of the formula (I) in good yield and high purity.

SUMMARY OF THE INVENTION

Accordingly, the present invention provides an improved process for the preparation of cefixime of formula (I), which comprises the steps of:

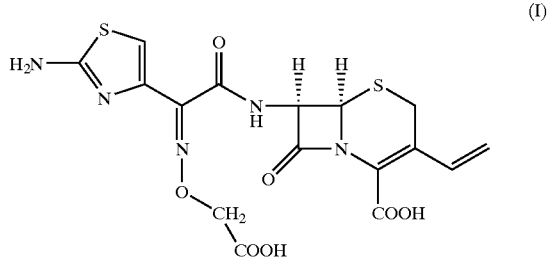

i. dissolving the ester compound of formula (II)

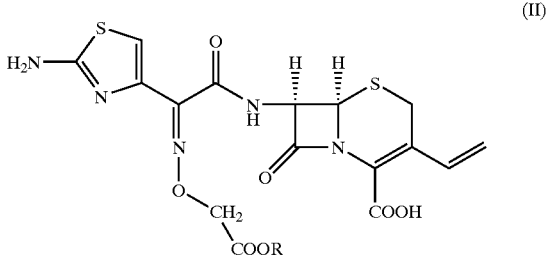

wherein R represents ($C_1$–$C_4$) alkyl group; in water/ water immiscible solvent using sodium bicarbonate at a temperature in the range of 0° C. to 35° C., (ii) hydrolysing step (i) mixture with sodium hydroxide at a temperature in the range of 0° C. to 25° C. and (iii) acidifying the resultant mass to pH 2.3 to 3.0 with dilute acid in the presence or absence of solvent at a temperature in the range of 10° C. to 45° C., to isolate the cefixime of the formula (I).

DETAILED DESCRIPTION OF THE INVENTION

In an embodiment of the present invention ($C_1$–$C_4$) alkyl group is selected from methyl, ethyl, propyl, iso-propyl, n-butyl, t-butyl and sec-butyl group.

In another embodiment of the present invention the water immisible solvent is selected from ethyl acetate, methylene chloride and ethylene dichloride.

In still another embodiment of the present invention the product may be isolated by adjusting pH to 2.3 to 3.0, by using acid such as hydrochloric acid, sulphuric acid or orthophosphoric acid, more particularly to pH 2.5±0.05 in the presence or absence of solvent such as acetone at a temperature in the range of 10° C. to 45° C., more particularly from 30° C. to 40° C. to produce cefixime of formula (I) in pure form.

In another embodiment of the present invention, the cefixime of the formula (I) obtained is in trihydrate form.

In yet another embodiment of the present invention, the cefixime of the formula (I) obtained is a syn isomer.

The present invention is exemplified by the following example, which is provided for illustration only and should not be construed to limit the scope of the invention.

The compound of formula (II) is prepared according to the process described and claimed in applicants U.S. Pat. No. 6,388,070

EXAMPLE

Preparation of [6R-[6α,7β(Z)]]-7-[[(2-amino-4-thiazolyl)[(carboxymethoxy)imino]acetyl]amino]-3-vinyl-3-cephem-4-carboxylic acid To, [6R-[6α,7β(Z)]]-7-[[(2-amino-4-thiazolyl)[(methoxycarbonylmethoxy)imino]acetyl]amino]-3-vinyl-3-cephem-4-carboxylic acid compound of formula (II) (100 gm) in distilled water (1000 ml) and ethyl acetate (500 ml), sodium bicarbonate (19 gm) was added slowly at 24–26° C. till clear solution formation. The solution was cooled to 0–1° C. and 15% sodium hydroxide solution (180 ml) was added. The resultant solution was stirred at 6–8° C. till the completion of reaction. pH of the reaction mass was adjusted to 4.8–5.0 with 19% aqueous HCl acid solution. The aqueous layer was separated and subjected to carbon treatment. To the clear filtrate, mixture of water (580 ml) and acetone (670 ml) was added. The pH of solution was adjusted to 2.45 to 2.55 with 8–10% dilute HCl acid at 34–36° C. The reaction mass was slowly cooled to 1–3° C. and stirred for 120 minutes. The product obtained was filtered and washed the wet product with water (1000 ml) and dried under vacuum to get the title compound in pure form (97.5 gm).

Advantages

The use of sodium hydroxide in the process of the present invention has improved the colour of the cefixime obtained. Finally, the solubility of cefixime obtained by this process is also enhanced.

What is claimed is:

1. An improved process for the preparation cefixime of formula (I)

(I)

the said process comprising the steps of:
   i. dissolving the compound of formula (II)

(II)

wherein R represents ($C_1$–$C_4$) alkyl group; in water/water immisible solvent using sodium bicarbonate at a temperature in the range of 0° C. to the 35° C.,
   ii. hydrolyzing with sodium hydroxide at a temperature in the range of 0° C. to 25° C. and
   iii. acidifying the resultant mass to pH 2.3 to 3.0 with dilute acid in the presence or absence of solvent at a temperature in the range of 10° C. to 45° C., to isolate the compound of formula (I).

2. The process as claimed in claim 1, wherein the reaction temperature for step (i) is preferably in the range of 20° C. to 30° C.

3. The process as claimed in claim 1, wherein the water immisible solvent used in step (i) is selected from ethyl acetate, methylene chloride and ethylene dichloride.

4. The process as claimed in claim 1, wherein in step (iii) the pH for isolation is in the range of 2.5±0.05.

5. The process as claimed in claim 1, wherein the acid used for pH adjustment is selected from hydrochloric acid, sulphuric acid and orthophosphoric acid.

6. The process as claimed in claim 1, wherein in step (iii) the solvent used for isolation is acetone.

7. The process as claimed in claim 1, wherein the isolation is carried out at a temperature in the range of 30° C. to 40° C.

8. The process as claimed in claim 1, wherein cefixime of formula (I) is in trihydrate form.

* * * * *